United States Patent
Kim et al.

(10) Patent No.: US 9,225,365 B2
(45) Date of Patent: Dec. 29, 2015

(54) SAMPLING METHOD, APPARATUS, PROBE, RECEPTION BEAMFORMING APPARATUS, AND MEDICAL IMAGING SYSTEM PERFORMING THE SAMPLING METHOD

(71) Applicant: SAMSUNG ELECTRONICS CO., LTD., Suwon-si (KR)

(72) Inventors: Bae-hyung Kim, Yongin-si (KR); Kyung-il Cho, Seoul (KR); Dong-wook Kim, Seoul (KR); Jong-keun Song, Yongin-si (KR); Seung-heun Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 13/665,359

(22) Filed: Oct. 31, 2012

(65) Prior Publication Data
US 2013/0109969 A1    May 2, 2013

(30) Foreign Application Priority Data
Oct. 31, 2011    (KR) .................. 10-2011-0112493

(51) Int. Cl.
| | |
|---|---|
| A61B 8/00 | (2006.01) |
| H04B 1/06 | (2006.01) |
| G01S 7/52 | (2006.01) |
| G10K 11/34 | (2006.01) |
| A61B 8/08 | (2006.01) |
| G01S 15/89 | (2006.01) |

(52) U.S. Cl.
CPC ...... *H04B 1/06* (2013.01); *A61B 8/483* (2013.01); *A61B 8/5207* (2013.01); *G01S 7/52034* (2013.01); *G01S 15/8915* (2013.01); *G10K 11/341* (2013.01); *A61B 8/4488* (2013.01); *G01S 15/8927* (2013.01); *G01S 15/8979* (2013.01); *G01S 15/8993* (2013.01)

(58) Field of Classification Search
CPC ............ A61B 8/06; A61B 8/46; A61B 8/461; A61B 8/467; A61B 8/483–8/486; A61B 8/4488; A61B 8/5207; G10K 11/35; G10K 11/352; G10K 11/36; G10K 11/341; H04B 1/06; G01S 15/8979; G01S 15/8993; G01S 15/8915; G01S 15/8927; G01S 7/52034
USPC ......................... 600/437–469; 382/128–132
See application file for complete search history.

(56) References Cited

U.S. PATENT DOCUMENTS

| | | | | |
|---|---|---|---|---|
| 6,016,825 | A * | 1/2000 | Andersson ...................... 137/88 |
| 6,110,116 | A * | 8/2000 | Wright et al. ................. 600/447 |
| 6,520,915 | B1 * | 2/2003 | Lin et al. ....................... 600/453 |
| 2012/0053461 | A1 * | 3/2012 | Li et al. ........................ 600/441 |

FOREIGN PATENT DOCUMENTS

| | | |
|---|---|---|
| KR | 10-2007-0089101 A | 8/2007 |
| KR | 10-2008-0096124 A | 10/2008 |
| KR | 10-2009-0080037 A | 7/2009 |
| KR | 10-1055582 B1 | 8/2011 |

* cited by examiner

*Primary Examiner* — Sanjay Cattungal
(74) *Attorney, Agent, or Firm* — Sughrue Mion, PLLC

(57) ABSTRACT

A sampling method for generating a diagnostic image of an object is provided. The sampling method may include receiving an echo signal reflected from an object; sampling the received echo signal by using a sampling frequency and storing the I component data and the Q component data extracted according to a result of the sampling.

18 Claims, 6 Drawing Sheets

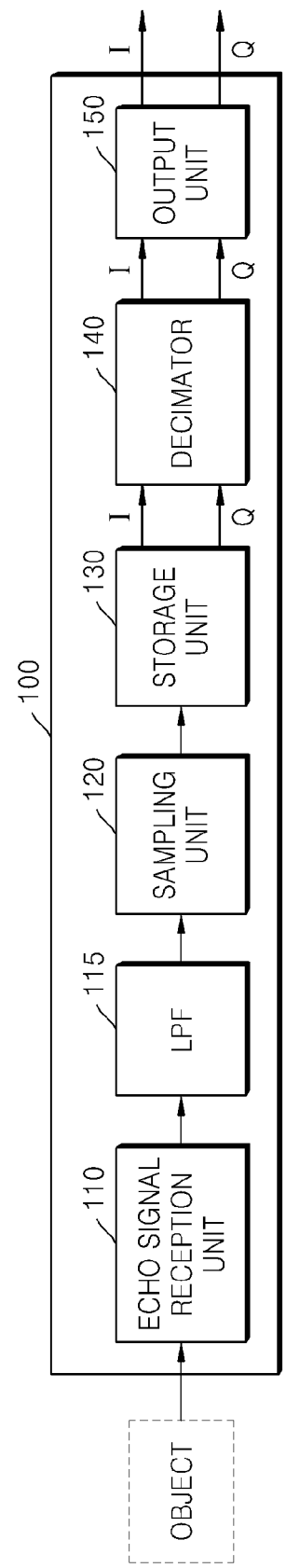

US 9,225,365 B2

SAMPLING METHOD, APPARATUS, PROBE, RECEPTION BEAMFORMING APPARATUS, AND MEDICAL IMAGING SYSTEM PERFORMING THE SAMPLING METHOD

CROSS-REFERENCE TO RELATED APPLICATIONS

This application claims priority from Korean Patent Application No. 10-2011-0112493, filed on Oct. 31, 2011, in the Korean Intellectual Property Office, the disclosure of which is incorporated herein in its entirety by reference.

BACKGROUND

1. Field

Methods and apparatuses consistent with the exemplary embodiments relate to a sampling method, an apparatus, a probe, a reception beamforming apparatus, and a medical imaging system performing the sampling method.

2. Description of the Related Art

Real-time 3-dimensional (3D) diagnostic images may be generated using echo signals reflected from an object. The real-time 3D diagnostic images for the object are provided so that a user easily recognizes anatomic information regarding internal body parts of the object, and thus may improve diagnostic convenience and accuracy for the user. As such, real-time 3D diagnostic images including volume information regarding an object need to be generated through a sampling operation for digitizing echo signals reflected from the object.

SUMMARY

According to an aspect of an exemplary embodiment, there is provided efficient sampling methods, apparatuses, probes, reception beamforming apparatuses, and medical imaging systems performing the sampling methods. There are also provided non-transitory computer-readable recording media having recorded thereon a computer program for executing the efficient sampling methods. Additional aspects will be set forth in part in the description which follows and, in part, will be apparent from the description, or may be learned by practice of the presented exemplary embodiments.

According to an aspect of an exemplary embodiment, a sampling method includes receiving an echo signal reflected from an object; sampling the received echo signal by using a sampling frequency to extract in-phase (I) component data and quadrature (Q) component data; and alternately arranging and storing the I component data and the Q component data extracted according to a result of the sampling.

According to another aspect of an exemplary embodiment, a computer-readable recording medium has recorded thereon a computer program for executing the sampling method.

According to another aspect of an exemplary embodiment, a sampling apparatus includes an echo signal reception unit which receives an echo signal reflected from an object; a sampling unit which samples the received echo signal by using a sampling frequency to extract in-phase (I) component data and quadrature (Q) component data; and a storage unit which alternately arranges and stores the I component data and the Q component data extracted according to a result of the sampling.

According to another aspect of an exemplary embodiment, a probe includes a transducer-array which receives an echo signal from an object; and a sampling unit which samples an echo signal received from the transducer-array by using a sampling frequency to extract I component data and Q component data, and outputs the I component data and the Q component data extracted according to a result of the sampling.

According to another aspect of an exemplary embodiment, a reception beamforming apparatus includes a sampling unit which samples an echo signal for each of a plurality of channels by using a sampling frequency to extract I component data and Q component data, and outputs I component data and Q component data for each of the plurality of channels extracted according to a result of the sampling; an interpolator which interpolates the output I component data and Q component data for each of the plurality of channels; and a beamformer which performs beamforming with respect to I component data and the Q component data for each of the plurality of channels obtained by the interpolation in the interpolator to generate a beamformed signal for the I component data and a beamformed signal for the Q component data.

According to another aspect of an exemplary embodiment, a medical imaging system includes a probe which samples an echo signal reflected from an object by using a sampling frequency to extract I component data and Q component data, and outputs I component data and Q component data extracted according to a result of the sampling; and a diagnostic image generation apparatus which generates a diagnostic image of the object by using the output I component data and the output Q component data.

BRIEF DESCRIPTION OF THE DRAWINGS

The foregoing and/or other aspects will become apparent and more readily appreciated from the following description of exemplary embodiments, taken in conjunction with the accompanying drawings of which:

FIG. 3A is a block diagram of a sampling apparatus according to an exemplary embodiment;

DETAILED DESCRIPTION OF EXEMPLARY EMBODIMENTS

Figure 1:
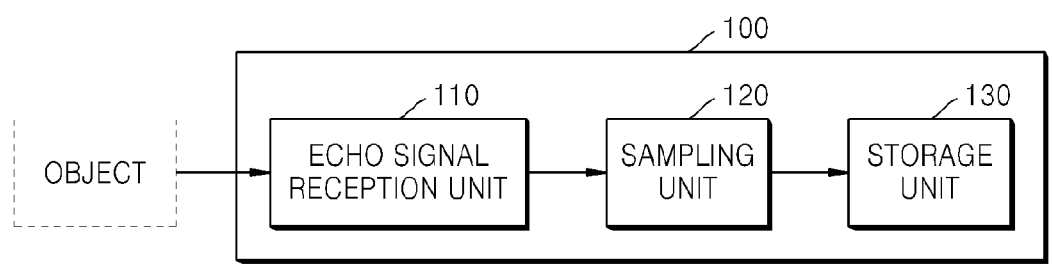
FIG. 1 is a block diagram of a sampling apparatus according to an exemplary embodiment.

Reference will now be made in detail to exemplary embodiments, examples of which are illustrated in the accompanying drawings, wherein like reference numerals refer to the like elements throughout. In this regard, the exemplary embodiments may have different forms and should not be construed as being limited to the descriptions set forth herein. Accordingly, the exemplary embodiments are merely described below, by referring to the figures, to explain aspects of the present description.

FIG. 1 is a block diagram of a sampling apparatus 100 according to an exemplary embodiment. Referring to FIG. 1, the sampling apparatus 100 includes an echo signal reception unit 110, a sampling unit 120, and a storage unit 130.

FIG. 1 illustrates only components of the sampling apparatus 100 that are associated with the present exemplary embodiment. Accordingly, it will be understood by one of ordinary skill in the art to which the present exemplary embodiment pertains that the sampling apparatus 100 may further include general-use components other than the components illustrated in FIG. 1. In addition, each of the echo signal reception unit 110 and the sampling unit 120 of the sampling apparatus 100 may correspond to one processor or a plurality of processors.

According to the present exemplary embodiment, the sampling apparatus 100 samples an echo signal reflected from an object. The sampling may denote an operation of extracting a plurality of pieces of digital data from an analog signal by using a sampling frequency, but the sampling is not limited thereto.

The echo signal reception unit 110 receives the echo signal reflected from the object. The echo signal reflected from the object may be an ultrasonic signal which is a radio frequency (RF) signal reflected from the object, but the echo signal is not limited thereto. The echo signal may be any signal obtained by reflecting a signal transmitted to the object.

According to the present exemplary embodiment, the object may be an organ of a human body, such as, a liver, an abdominal area, a heart, or a brain. According to the present exemplary embodiment, the echo signal reception unit 110 may be a transducer that receives the echo signal from the object, but the echo signal reception unit 110 is not limited thereto.

The sampling unit 120 samples the echo signal received by the echo signal reception unit 110, by using a sampling frequency for extracting in-phase (I) component data and quadrature (Q) component data.

For example, the sampling unit 120 may sample the echo signal to alternately extract I component data and Q component data for the echo signal. The alternate extraction of the I component data and Q component data may be such that the data extracted according to a sampling result is I component data and Q component data in sequence or Q component data and I component data in sequence.

The sampling unit 120 may also sample the echo signal to alternately and sequentially extract the I component data and the Q component data for the echo signal. The terminology "sequentially" may denote a sequence in which sampling is performed in the sampling unit 120. This sequential extraction will be described in detail later with reference to Equations 1-5.

Accordingly, as the sampling unit 120 samples the echo signal by using the sampling frequency, the I component data and Q component data of the echo signal may be directly extracted from the echo signal. The direct extraction of the I component data and Q component data from the echo signal denotes an operation in which the I component data and Q component data are extracted by sampling the echo signal without performing demodulation on the echo signal.

In more detail, when a demodulation operation using a demodulator is performed to extract I component data and Q component data for an echo signal, the demodulator needs to include hardware such as a cosine look-up table, a sine look-up table, and a multiplier. On the other hand, the sampling unit 120 according to the present exemplary embodiment may directly extract the I component data and the Q component data from the echo signal by using a predetermined sampling frequency without performing demodulation on the echo signal, thereby reducing hardware complexity of the sampling apparatus 100. The predetermined sampling frequency may be a sampling frequency for extracting the I component data and Q component data for the echo signal.

For example, the sampling frequency for extracting the I component data and the Q component data may be a minimum sampling frequency based on the sampling theory. A minimum sampling frequency may be a frequency corresponding to 4 times a center frequency of a transducer for transmitting a transmission signal to an object, a frequency corresponding to 4 times the frequency of the echo signal received by the echo signal reception unit 110, or a frequency corresponding to 4 times the frequency of the transmission signal.

In more detail, the minimum sampling frequency based on the sampling theory may be a frequency corresponding to 4 times the center frequency of a transducer for transmitting a transmission signal to an object. The transducer may be included in the echo signal reception unit 110 of the sampling apparatus 100, but the location of the transducer is not limited thereto. The transducer may exist outside the echo signal reception unit 110.

In more detail, the transducer transmits the transmission signal to the object and receives the echo signal reflected from the object. The frequencies of the transmission signal and the echo signal may be the center frequency of the transducer or a frequency similar to the center frequency of the transducer, but the frequencies of the transmission signal and the echo signal are not limited thereto.

For example, when a transducer having a center frequency of f1 transmits a signal to an object, the frequency of a transmission signal and the frequency of an echo signal reflected from the object may be the center frequency f1 of the transducer. The frequency of the transmission signal and the frequency of the echo signal may further include a harmonic frequency of the center frequency of f1 of the transducer.

For example, when a transducer having a center frequency of f1 transmits a signal to an object, the frequency of a transmission signal and the frequency of an echo signal reflected from the object may be a frequency similar to the center frequency of f1 of the transducer, but not limited thereto. The frequency of the transmission signal and the frequency of the echo signal may further include a harmonic frequency of a fundamental frequency which is a frequency similar to the center frequency f1 of the transducer. In other words, while a transmission signal is being transmitted and an echo signal is being reflected from an object, the transmission signal and the echo signal may be transformed. Accordingly, the transmission signal and the echo signal may not have the center frequency of f1 of the transducer, but a frequency similar to the center frequency of f1.

In this case, a user of the sampling apparatus 100 may select and use the fundamental frequency or harmonic frequency of the transmission signal as the frequency of the transmission signal, and select and use the fundamental frequency or harmonic frequency of the echo signal as the frequency of the echo signal.

For convenience of explanation, a case where the center frequency of the transducer is equivalent to the frequency of the echo signal or the frequency of the transmission signal is illustrated, but not limited thereto.

When the frequency of a transmission signal, the center frequency of a transducer for transmitting the transmission signal, or the frequency of an echo signal is f0, the bandwidth of the transmission signal or the echo signal is 2f0 or less. Thus, a maximum frequency for the transmission signal or the echo signal may be 2f0 or less. Thus, the minimum sampling frequency based on the sampling theory may be 4fo; that is 4 times the center frequency of the transducer, 4 times the frequency of the echo signal, or 4 times the frequency of the transmission signal.

Accordingly, the sampling unit 120 according to the present exemplary embodiment may sample the echo signal by using a sampling frequency that corresponds to 4 times one of the center frequency of the transducer, the frequency of the echo signal, and the frequency of the transmission signal.

A process of extracting the I component data and Q component data for the echo signal as the sampling unit 120 samples the echo signal by using a sampling frequency that corresponds to 4 times one of the center frequency of a transducer transmitting a transmission signal, the frequency of an echo signal, and the frequency of the transmission signal, will now be described using examples.

The echo signal input to the sampling unit 120 may be expressed as in Equation 1 by using an I component signal and a Q component signal:

$$r(t) = r_I(t)\cos(2\pi f_r t) + r_Q(t)\sin(2\pi f_r t) \quad \text{[Equation 1]}$$

where r(t) may denote the echo signal according to time, t may denote the time, $f_r$ may denote a frequency of the echo signal, $r_I(t)$ may denote the I component signal, and $r_Q(t)$ may denote the Q component signal. In this case, the frequency $f_r$ of the echo signal may be the center frequency f0 of the transducer or the frequency $f_r$ of the transmission signal.

Although the echo signal has only the frequency $f_r$ which is a fundamental frequency in Equation 1, the frequency of the echo signal is not limited thereto. The echo signal may further include a harmonic frequency for the fundamental frequency $f_r$. In this case, a user may select one of the fundamental frequency $f_r$ and the harmonic frequency as the frequency of the echo signal.

When the sampling unit 120 samples the echo signal according to a sampling period $T_s$, the echo signal may be expressed as in Equation 2:

$$r(nT) = r_I(nT_s)\cos(2\pi f_r nT_s) + r_Q(nT_s)\sin(2\pi f_r nT_s) \quad \text{[Equation 2]}$$

where $T_s$ may denote a sampling period and n denotes the number of times of sampling. As described above, since the sampling unit 120 performs sampling by using a sampling frequency $4f_r$ corresponding to 4 times the frequency of the echo signal, the sampling period $T_s$ may be expressed as in Equation 3:

$$T_s = \frac{1}{4f_r} \quad \text{[Equation 3]}$$

Accordingly, as Equation 3 is substituted into Equation 2, an echo signal obtained by the sampling in the sampling unit 120 may be expressed as in Equation 4:

$$r(nT_s) = r_I(nT_s)\cos\left(\frac{n\pi}{2}\right) + r_Q(nT_s)\sin\left(\frac{n\pi}{2}\right) \quad \text{[Equation 4]}$$

Accordingly, the I component data and Q component data alternately and sequentially extracted according to a result of the sampling performed by the sampling unit 120 may be expressed as in Equation 5:

$$\begin{aligned}
r(0) &= r_I(0) \\
&= I(0) \\
r(T_s) &= r_Q(T_s) \\
&= Q(1) \\
r(2T_s) &= -r_I(2T_s) \\
&= -I(2) \\
r(3T_s) &= -r_Q(3T_s) \\
&= -Q(3) \\
r(4T_s) &= r_I(4T_s) \\
&= I(4) \\
r(5T_s) &= r_Q(5T_s) \\
&= Q(5) \\
r(6T_s) &= -r_I(6T_s) \\
&= -I(6) \\
r(7T_s) &= -r_Q(7T_s) \\
&= -Q(7) \\
&\vdots
\end{aligned} \quad \text{[Equation 5]}$$

where I(0) may denote I component data extracted according to a first sampling result, Q(1) may denote Q component data extracted according to a second sampling result, −I(2) may denote I component data extracted according to a third sampling result. In this way, the I component data and the Q component data may be alternately and sequentially extracted according to the result of the sampling performed by the sampling unit 120.

As described above, the sampling unit 120 may perform interleaved down-sampling with respect to the echo signal. Accordingly, each of the I component data and the Q component data extracted according to the sampling in the sampling unit 120 may be data down-sampled at a sampling rate of 2f0 corresponding to twice the center frequency of the transducer, the frequency of the echo signal, or the frequency of the transmission signal.

The sampling frequency according to the present exemplary embodiment is not limited to the minimum sampling frequency, the frequency corresponding to 4 times the center frequency of the transducer, the frequency corresponding to 4 times the frequency of the echo signal, or the frequency corresponding to 4 times the frequency of the transmission signal, and may be any frequency capable of extracting the I component data and the Q component data for the echo signal.

The sampling unit 120 according to the present exemplary embodiment may be an analog to digital converter (ADC) for converting the echo signal which is an analog signal into the I and Q component data which is a digital signal, but the sampling unit 120 is not limited thereto.

The storage unit 130 alternately arranges and stores the I component data and the Q component data extracted according to the result of the sampling in the sampling unit 120. For example, the storage unit 130 may sequentially alternate the I component data and the Q component data, such as the I component data I(0), the Q component data Q(1), the I component data −I(2), and the Q component data −Q(3) as shown in Equation 5, and store the alternating I and Q component data.

In more detail, since the I component data and the Q component data are alternately and sequentially extracted according to the result of the sampling in the sampling unit 120, the storage unit 130 may store alternately and sequentially the I component data and the Q component data even when the I component data and the Q component data are received via a single port. Accordingly, the storage unit 130 may be a one-port memory including a single input port.

Therefore, the storage unit 130 according to the present exemplary embodiment receives the I component data and the Q component data via a single port and sequentially and alternately arranges and stores the received I and Q component data. This storage of the sequentially alternating I and Q component data will be described below with reference to FIG. 2.

In addition, since the I component data and the Q component data output from the storage unit 130 may be a base-band signal, when a diagnostic image is generated from a signal stored in the storage unit 130, a data rate for transmitting the I component data and the Q component data may be reduced.

The storage unit 130 according to the present exemplary embodiment is a typical storage medium, and examples of the storage unit 130 may include a hard disk drive (HDD), a read only memory (ROM), a random access memory (RAM), a flash memory, and a memory card.

Accordingly, the sampling apparatus 100 according to the present exemplary embodiment may directly extract the I component data and the Q component data of the echo signal by sampling the echo signal by using the sampling frequency for extracting the I component data and the Q component data.

Therefore, the sampling apparatus 100 may sample the echo signal without a demodulator and thus may result in reduced hardware complexity and more efficient sampling of the echo signal.

A front-end device that is used to generate the diagnostic image of the object may be included in a probe by using the sampling apparatus 100 according to the present exemplary embodiment, but the front-end device is not limited thereto. The front end device may be included in a general-use computer system, a user terminal, or the like such as a mid-end device or a back-end device.

Figure 2:
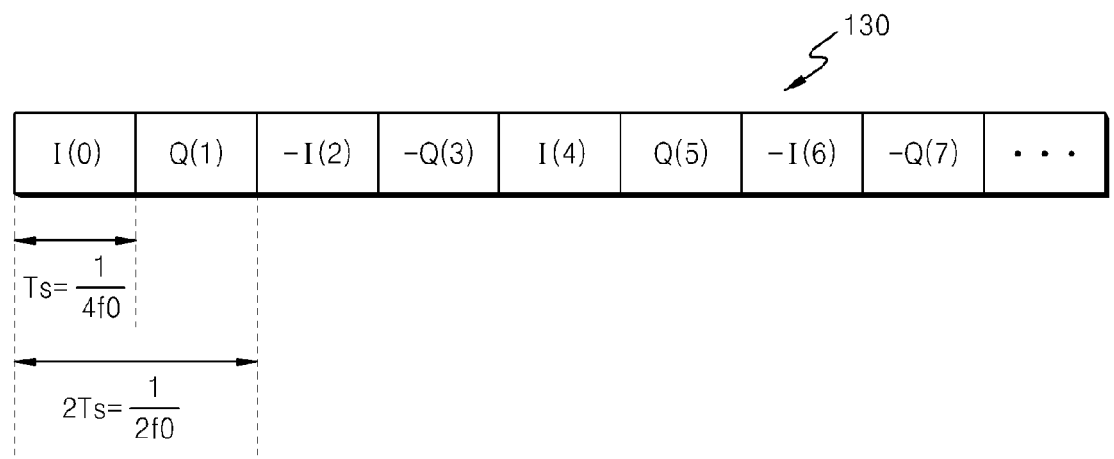
FIG. 2 illustrates an example of a method in which a storage unit included in the sampling apparatus illustrated in FIG. 1 stores in-phase (I) component data and quadrature (Q) component data.

FIG. 2 illustrates an example of a method in which the storage unit 130 of FIG. 1 stores the I component data and the Q component data.

Referring to FIG. 2, the storage unit 130 sequentially alternates the I component data and the Q component data, such as the I component data I(0), the Q component data Q(1), the I component data −I(2), and the Q component data −Q(3) as shown in Equation 5, and stores the alternating I and Q component data.

The I component data and the Q component data may be extracted by performing interleaved down-sampling on the echo signal at the sampling frequency of 4f0 that corresponds to 4 times the center frequency of the transducer, 4 times the frequency of the echo signal, or 4 times the frequency of the transmission signal. Each of the I component data and the Q component data may be data down-sampled at a sampling rate of 2f0 that corresponds to twice the center frequency of the transducer, the frequency of the transmission signal, or the frequency of the echo signal.

The storage unit 130 according to the present exemplary embodiment receives the I component data and the Q component data via a single port and sequentially and alternately arranges and stores the received I component data and the received Q component data.

Since the storage unit 130 sequentially and alternately arranges and stores the received I component data and the received Q component data, the I component data and the Q component data stored in the storage unit 130 may be read out in an interleaving manner and thus the read-out I component data and the read-out Q component data may be distinguishably used.

FIG. 3A is a block diagram of a sampling apparatus 100 according to another exemplary embodiment. Referring to FIG. 3A, the sampling apparatus 100 includes an echo signal reception unit 110, a low pass filter (LPF) 115, a sampling unit 120, a storage unit 130, a decimator 140, and an output unit 150.

The sampling apparatus 100 of FIG. 3 is merely exemplary, and is not limited to the components illustrated in FIG. 3A. Matters described above with reference to FIG. 1 may be applied to the sampling apparatus 100 of FIG. 3A, so a detailed description thereof will not be provided here.

The echo signal reception unit 110 receives an echo signal reflected from an object. The echo signal reception unit 110 according to the present exemplary embodiment may include a low noise amplifier (LNA) (not shown) for reducing noise of the echo signal, and a variable gain amplifier (VGA) (not shown) for controlling a gain value according to a received signal or a preamplifier (not shown). The VGA may be a time gain compensator (TGC) that compensates for a gain depending on a distance between the transducer and a focusing point on an object, but the VGA is not limited thereto.

The LPF 115 performs low pass filtering (LPF) on the echo signal received by the echo signal reception unit 110. For example, the LPF 115 may be an anti-aliasing filter for preventing aliasing from occurring due to a high frequency component of a signal. However, the LPF 115 is not limited thereto. The LPF 115 may be combined with the echo signal reception unit 110 to constitute a single ADC.

The sampling unit 120 samples an echo signal obtained by the filtering of the LPF 115, by using a sampling frequency for extracting I component data and Q component data. Accordingly, the sampling unit 120 may directly extract the I component data and the Q component data from the echo signal obtained by the filtering of the LPF 115.

The storage unit 130 alternately arranges and stores the I component data and the Q component data extracted according to the result of the sampling in the sampling unit 120.

The decimator 140 decimates the I component data and the Q component data stored in the storage unit 130. For example, the decimator 140 may perform down-sampling at an interval greater than a sampling interval based on the sampling performed by the sampling unit 120. In other words, when the sampling unit 120 performs sampling by using the sampling frequency of 4f0, the decimator 140 may perform down-sampling by using a sampling frequency of 4fo or less (for example, 2f0).

According to the present exemplary embodiment, the decimator 140 may be a decimation filter that performs down-sampling, but the decimator 140 is not limited thereto. The decimator 140 may perform decimation by reading the I component data and the Q component data stored in the storage unit 130 in an interleaving manner.

Therefore, the decimator 140 may distinguishably read the I component data and the Q component data from the storage unit 130 including a single input port, and perform decimation on each of the read-out I component data and the read-out Q component data.

The decimator 140 according to the present exemplary embodiment may reduce the number of times of sampling by reducing a data rate, but may increase hardware complexity because operations subsequent to the decimation in the decimator 140 may need an LPF (not shown). Therefore, the sampling apparatus 100 according to the present exemplary embodiment may determine whether the decimator 140 is to be used, in consideration of the amount of data and the hardware complexity.

The output unit 150 outputs I component data and Q component data obtained by the decimation performed in the decimator 140. At this time, the output unit 150 may output data through wire transmission (for example, a PCI, a PCI-express, or a USB), wireless transmission (for example, Wifi or Zigbee), a data/control bus, or the like. For example, the output unit 150 outputs the stored I component data and Q component data, or data decimated from the stored I component data and Q component data via wireless transmission. The stored I component data and Q component data may be stored in the storage unit 130 and the data decimated from the stored I component data and Q component data may be obtained from decimator 140. In this regard, the stored I component data and Q component data, or the data decimated from the stored I component data and Q component data may be transmitted from the sampling apparatus 100 to a beamformer (not shown), an interpolator (not shown), a diagnostic image generation apparatus (not shown), or a computing apparatus (not shown) via wireless transmission.

The data output by the output unit 150 may be transmitted to an external device such as a general-use computer system, a portable terminal, a facsimile machine, a medical imaging system, or an ultrasonic imaging apparatus.

Since the sampling apparatus 100 according to the present exemplary embodiment performs sampling by using the sampling frequency for extracting the I component data and the Q component data from the echo signal, hardware complexity may be reduced. In addition, since the sampling apparatus 100 according to the present exemplary embodiment performs decimation, the amount of data to be transmitted may be reduced.

Thus, the sampling apparatus 100 may be miniaturized, and the sampling apparatus 100 may transmit in real time data that is obtained by the sampling performed on the echo signal reflected from the object. Therefore, the sampling apparatus 100 according to the present exemplary embodiment may have a compact design, and accordingly, the sampling apparatus 100 according to the present exemplary embodiment may be included in a front-end device or a probe.

Figure 3B:
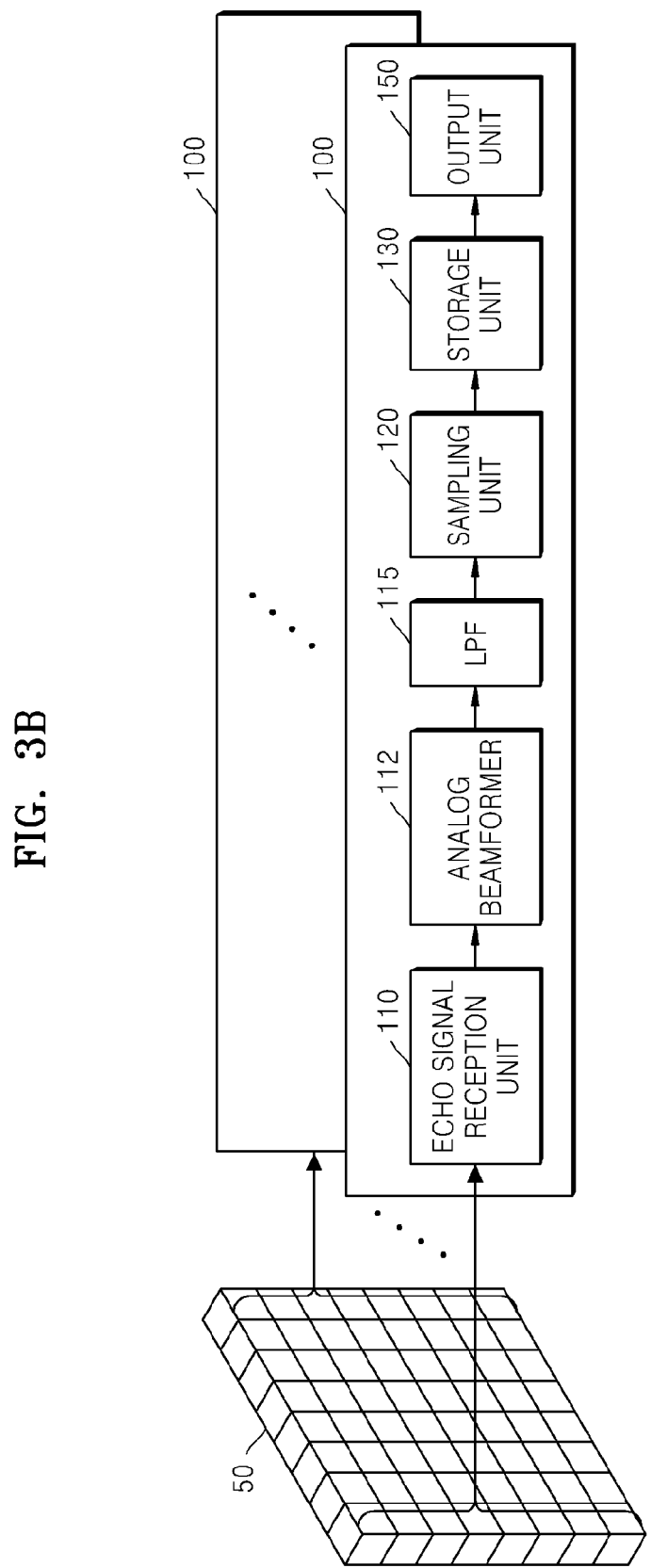
FIG. 3B is a block diagram of a sampling apparatus according to an exemplary embodiment.

FIG. 3B is a block diagram of a sampling apparatus 100 according to another exemplary embodiment. Referring to FIG. 3B, the sampling apparatus 100 includes an echo signal reception unit 110, an analog beamformer 112, an LPF 115, a sampling unit 120, a storage unit 130, and an output unit 150.

The sampling apparatus 100 of FIG. 3B is merely exemplary, and is not limited to the components illustrated in FIG. 3B. Matters described above with reference to FIG. 1 may be applied to the sampling apparatus 100 of FIG. 3B, so a detailed description thereof will not be provided here.

The sampling apparatus 100 of FIG. 3B is the same as the sampling apparatus 100 of FIG. 3A except that the analog beamformer 112 is further included and the decimator 140 is excluded, so a detailed description thereof will not be provided here.

The echo signal reception unit 110 receives an echo signal reflected from an object from a transducer array 50.

The analog beamformer 112 performs analog beamforming with respect to the echo signal output from the echo signal reception unit 110. When the transducer-array 50 is a 64×64 transducer-array formed of 64 sub-arrays, the echo signal reception unit 110 may receive echo signals of 64 channels, and the analog beamformer 112 may combine the echo signals of 64 channels to generate and output an echo signal corresponding to a single channel.

In this case, the analog beamformer 112 may perform the analog beamforming according to time delay values used in a transmission signal. The time delay values according to the present exemplary embodiment may be time delay values that depend on a distance between the transducer-array 50 transmitting the transmission signal and a focusing point on the object, but the time delay values are not limited thereto.

Because sampling apparatus 100 of the present exemplary embodiment includes the analog beamformer 112, hardware complexity is reduced by not requiring a separate sampling apparatus for each transducer included in transducer array 50.

The LPF 115 performs LPF on an echo signal output from the analog beamformer 112, and the sampling unit 120 samples an echo signal obtained by the filtering of the LPF 115, by using a sampling frequency for extracting I component data and Q component data. Accordingly, the sampling unit 120 may directly extract the I component data and the Q component data from the echo signal obtained by the filtering.

The storage unit 130 alternately arranges and stores the I component data and the Q component data extracted according to the result of the sampling performed in the sampling unit 120, and the output unit 150 outputs the I component data and the Q component data stored in the storage unit 130.

As illustrated in FIG. 3B, the number of the sampling apparatuses 100 according to the present exemplary embodiment may be equal to the number of sub-arrays of the transducer-array 50. When the transducer-array 50 is a 64×64 transducer-array formed of 64 sub-arrays, 64 sampling apparatuses 100 may be provided to sample echo signals respectively output from the 64 sub-arrays.

Accordingly, sampling for generating a high resolution diagnostic image may be performed while reducing the hardware complexity.

Figure 4A:
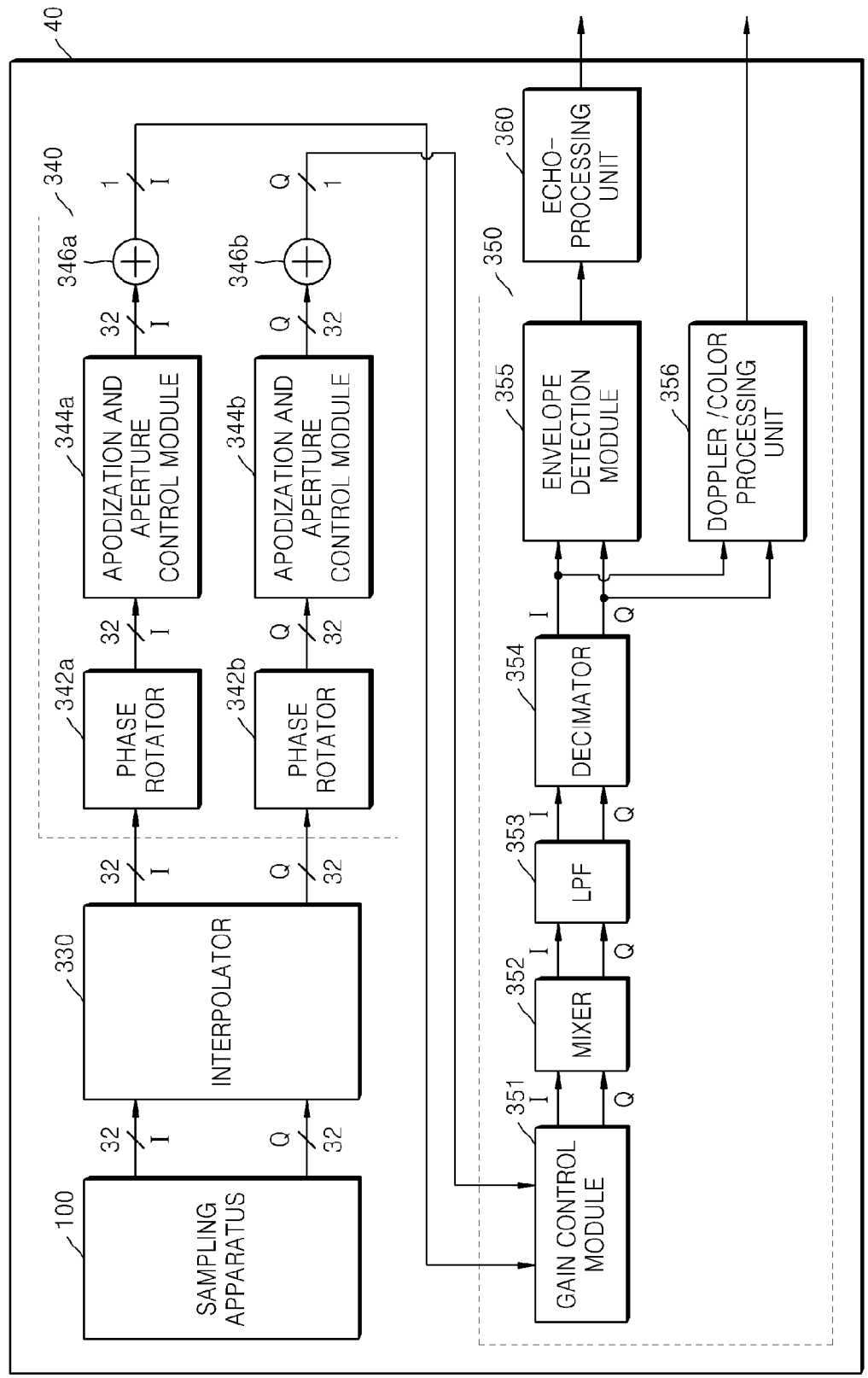
FIG. 4A is a block diagram of a reception beamforming apparatus according to an exemplary embodiment.
Figure 4B:
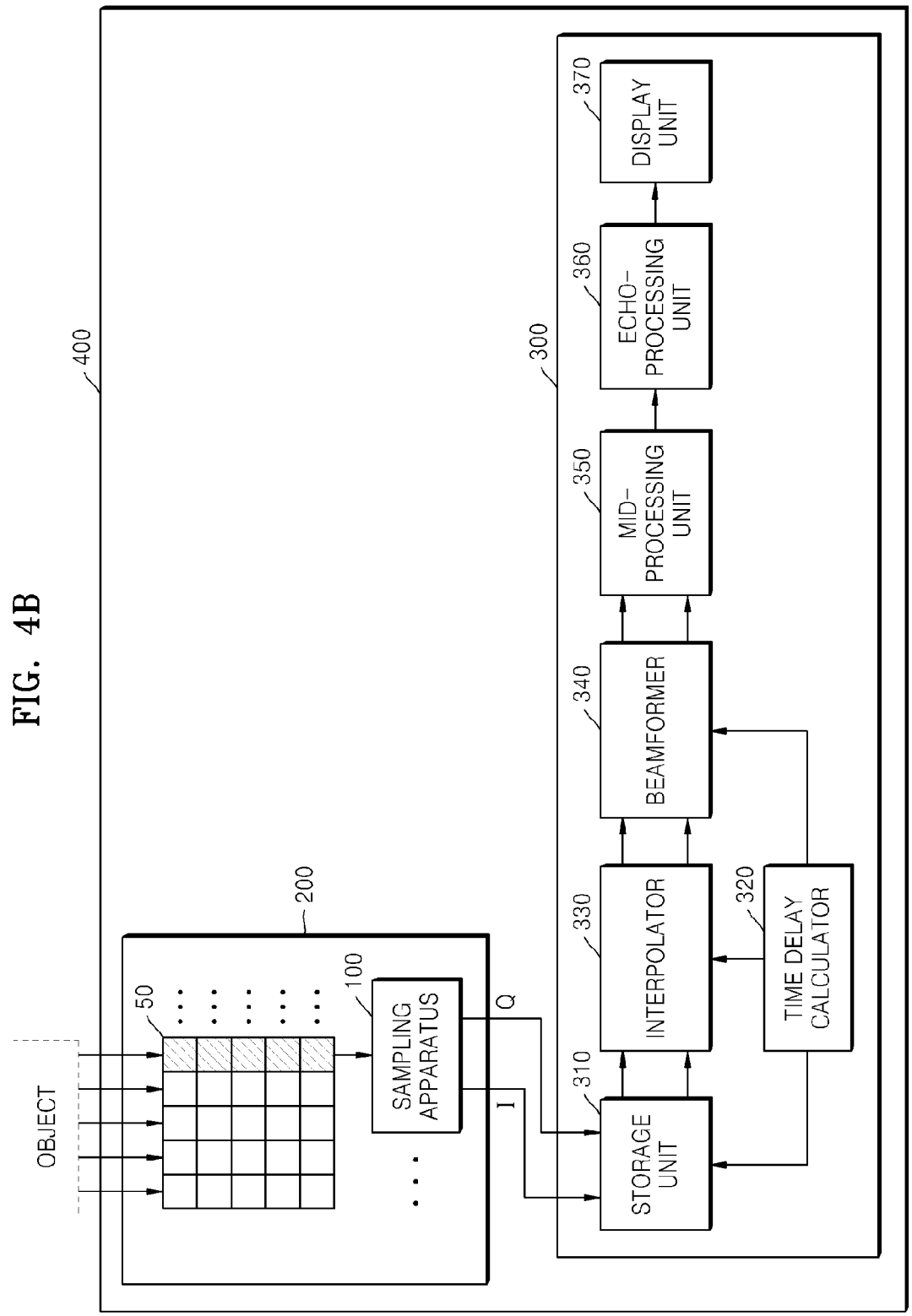
FIG. 4B is a block diagram of a diagnosis system according to an exemplary embodiment.

FIG. 4A is a block diagram of a reception beamforming apparatus 40 according to an exemplary embodiment. Referring to FIG. 4B, the reception beamforming apparatus 40 includes a sampling apparatus 100, an interpolator 330, a beamformer 340, a mid-processing unit 350, and an echo-processing unit 360. The beamformer 340 includes phase rotators 342a and 342b, apodization and aperture control modules 344a and 344b, and combiners 346a and 346b. The mid-processing unit 350 includes a gain control module 351, a mixer 352, an LPF 353, a decimator 354, an envelope detection module 355, and a Doppler/color processing unit 356. A module according to the present exemplary embodiment may be hardware, software for driving the hardware, or a combination thereof.

The sampling apparatus 100 of FIG. 4A may correspond to any one of the sampling apparatuses 100 of FIGS. 1, 3A, and 3B. Accordingly, matters described above with reference to FIGS. 1, 3A, and 3B may be applied to the sampling apparatus 100 of FIG. 4A, so a detailed description thereof will not be provided here.

FIG. 4A illustrates only components of the reception beamforming apparatus 40 that are associated with the present exemplary embodiment. Accordingly, it will be understood by one of ordinary skill in the art to which the present exemplary embodiment pertains that the reception beamforming apparatus 40 of FIG. 4A may further include general-use components other than the components illustrated in FIG. 4A.

The sampling apparatus 100 samples an echo signal received from a transducer-array by using a sampling frequency for extracting I component data and Q component data, and outputs the I component data and the Q component data extracted according to a result of the sampling to the interpolator 330.

For convenience of explanation, sampling apparatuses 100 respectively corresponding to 32 channels are provided in FIG. 4A, but the number of sampling apparatuses 100 is not limited thereto. In this case, the sampling apparatuses 100 output I component data and Q component data extracted from each of the 32 channels to the interpolator 330.

The interpolator 330 interpolates the I component data and the Q component data for each of the 32 channels output from the sampling apparatuses 100. For example, the interpolator 330 uses a time delay value for coarse delay. The time delay value may be calculated by a time delay calculator (not shown). An operation of the interpolator 330 that is associated with the time delay calculator will be described in more detail later with reference to FIG. 4B.

According to the present exemplary embodiment, a single interpolator 330 may be used to interpolate all of the I component data and the Q component data for each of the 32 channels.

Since each of the I component data and the Q component data extracted according to the sampling in the sampling unit 120 may be data down-sampled at a sampling rate of 2f0, which corresponds to twice the center frequency of a transducer, a frequency of an echo signal, or a frequency of transmission signal, the sampling apparatuses 100 according to the present exemplary embodiment may perform predetermined data processing with respect to the data down-sampled at the sampling rate of 2f0 by using a half band filter.

The beamformer 340 performs beamforming with respect to the I component data and the Q component data for each of the 32 channels output from the interpolator 330 to generate a single beamformed signal for the I component data and a single beamformed signal for the Q component data. For example, the beamformer 340 may perform beamforming by using the phase rotators 342a and 342b, the apodization and aperture control modules 344a and 344b, and the combiners 346a and 346b.

The phase rotators 342a and 342b perform phase rotation for fine delay with respect to the I component data and the Q component data for each of the 32 channels.

For example, the phase rotators 342a and 342b may perform beamforming with respect to the I component data and the Q component data for each of the 32 channels by using a time delay value for fine delay calculated by the time delay calculator (not shown). In more detail, the phase rotators 342a and 342b may perform beamforming with respect to the I component data and the Q component data for each of the 32 channels by converting the time delay value for fine delay into a phase and multiplying the I component data and the Q component data by the converted phase.

The phase rotators 342a and 342b may also perform phase rotation for recovering the center frequency of the transducer, the frequency of the echo signal, or the frequency of the transmission signal corresponding to a mixing frequency.

The apodization and aperture control modules 344a and 344b perform aperture control on, and apply an apodization window value to, the I component data and the Q component data for each of the 32 channels.

The apodization and aperture control modules 344a and 344b may apply the apodization window value to the I component data and the Q component data for each of the 32 channels while performing the aperture control on the I component data and the Q component data for each channel. Accordingly, the beamformer 340 according to the present exemplary embodiment may perform apodization for giving a weight to each channel, and may perform aperture control for a dynamic aperture growth.

The combiners 346a and 346b perform summation with respect to the I component data for each of the 32 channels and with respect to the Q component data for the 32 channels. Accordingly, the beamformer 340 may output the beamformed signal for the I component data and the beamformed signal for the Q component data. I component data for a plurality of channels and Q component data for the plurality of channels may be respectively combined into single I component data and single Q component data.

The mid-processing unit 350 may perform mid-processing on each of the beamformed signals for the I and Q component data output from the beamformer 340. For example, the mid-processing unit 350 may perform the mid-processing by using the gain control module 351, the mixer 352, the LPF 353, the decimator 354, the envelope detection module 355, and the Doppler/color processing unit 356.

The gain control module 351 controls a gain of each of the I component data and the Q component data.

The mixer 352 performs mixing with respect to the I component data and the Q component data output from the gain control module 351. For example, the mixer 352 may perform phase rotation based on a dynamic frequency variation with respect to each of a plurality of regions obtained by splitting according to predetermined depths, in order to compensate for a frequency variation that depends on a depth. Accordingly, the mixer 352 may be a dynamic local oscillator, but the mixer 352 is not limited thereto.

The LPF 353 performs LPF on the I component data and the Q component data output from the mixer 352. For example, the LPF 353 may perform LPF by using a fundamental frequency component, a harmonic frequency component, or the like of a signal output from the mixer 352, according to a center frequency selected by the mixer 352. In other words, the LPF 353 may use the fundamental frequency component, the harmonic frequency component, or the like of the signal output from the mixer 352 in order to obtain a signal component of a desired frequency band or remove a signal component of an undesired frequency band.

The decimator 354 decimates the I component data and the Q component data output from the LPF 353. For example, the decimator 354 may include a decimation filter and may be used to down-sample an up-sampled signal to a desired rate.

The envelope detection module 355 detects an envelope from the I component data and the Q component data output from the decimator 354, and the Doppler/color processing unit 356 performs Doppler/color processing on the I component data and the Q component data output from the decimator 354.

For example, the gain control module 351, the mixer 352, the LPF 353, the decimator 354, and the envelope detection module 355 may constitute a digital signal processor (DSP) for generating a brightness (B)-mode image.

For example, the gain control module 351, the mixer 352, the LPF 353, the decimator 354, and the Doppler/color processing unit 356 may constitute a DSP for generating a Doppler (D)-mode image and a color (C)-mode image.

The echo processing unit 360 may perform echo processing on data output from the mid-processing unit 350. For example, the echo processing unit 360 may include a digital scan converter (DSC) that performs scan conversion. Accordingly, data obtained by the scan conversion in the echo processing unit 360 may be a diagnostic image of the object.

FIG. 4B is a block diagram of a diagnostic system 400 according to an exemplary embodiment. Referring to FIG. 4B, the diagnostic system 400 may include a probe 200 and a diagnostic image generation apparatus 300. The probe 200 includes a transducer-array 50 and a sampling apparatus 100, and the diagnostic image generation apparatus 300 includes a storage unit 310, a time delay calculator 320, an interpolator 330, a beamformer 340, a mid-processing unit 350, an echo processing unit 360, and a display unit 370.

The sampling apparatus 100 of FIG. 4B may correspond to any one of the sampling apparatuses 100 of FIGS. 1, 3A, and 3B. Accordingly, matters described above with reference to FIGS. 1, 3A, and 3B may be applied to the sampling apparatus 100 of FIG. 4B, so a detailed description thereof will not be provided here.

FIG. 4B illustrates only components of the diagnostic system 400 that are associated with the present exemplary embodiment. Accordingly, it will be understood by one of ordinary skill in the art to which the present exemplary embodiment pertains that the diagnosis system 400 of FIG. 4B may further include general-use components other than the components illustrated in FIG. 4B.

In relation to this, for convenience of explanation, it is illustrated in FIG. 4B that the diagnostic system 400 includes a component for generating and displaying a diagnostic image by using an echo signal reflected from an object. However, the diagnosis system 400 may further include a component for transmitting a transmission signal to the object.

The probe 200 receives an echo signal from the object by using the transducer-array 50 and outputs a result of sampling performed on the echo signal reflected from the object by the sampling apparatus 100 to the diagnostic image generation apparatus 300.

The transducer-array 50 includes at least one transducer that receives the echo signal reflected from the object. The transducer according to the present exemplary embodiment converts an electrical signal into an ultrasonic signal, transmits the ultrasonic signal to the object, receives an ultrasonic signal reflected from the object, and re-converts the ultrasonic signal into an electrical signal. The ultrasonic signal reflected from the object or the electrical signal into which the ultrasonic signal reflected from the object is re-converted may be an echo signal.

In FIG. 4B, the transducer-array 50 is a 2D array-transducer for convenience of explanation, but the transducer-array 50 is not limited thereto. The transducer-array 50 may be a 1D array-transducer.

When the transducer-array 50 is a 1D array-transducer, the transducer-array 50 may output an echo signal for generating a 2D diagnostic image of a cross-section of the interior of the object. However, when a 3D diagnostic image is desired to be generated using a 1D array-transducer, volume information regarding the interior of the object is obtained while mechanically moving the 1D array-transducer.

As such, when a 3D diagnostic image is obtained through mechanical movement of a 1D array-transducer, performance in terms of a temporal resolution, such as a speed at which a diagnostic image is formed or a spatial resolution, may be restricted.

When the transducer-array 50 is a 2D array-transducer, the transducer-array 50 may output an echo signal for generating a 3D diagnostic image having volume information regarding the object. When the 2D array-transducer is used, an optimal spatial resolution may be obtained from a 3D image point on the object, and a real-time high-resolution 3D diagnosis image may be obtained by using an electrical switching method instead of a mechanical moving method.

However, when the 2D array-transducer is used, hardware complexity and the number of cables used to transmit an enormous amount of data in real time increase. Therefore, the sampling apparatus 100 according to the present exemplary embodiment may reduce hardware complexity by sampling the echo signal output from the transducer-array 50 to directly extract I component data and Q component data and performing reception beam focusing by using the I component data and the Q component data.

Although only a single sampling apparatus 100 is illustrated in FIG. 4B for convenience of explanation, sampling apparatuses 100 respectively corresponding to transducers included in the transducer-array 50 may be provided, or sampling apparatuses 100 respectively corresponding to a plurality of sub-arrays included in the transducer-array 50 may be provided. A channel according to the present exemplary embodiment may be a transducer included in the transducer-array 50, but the channel is not limited thereto.

A case where one sampling apparatus 100 corresponding to one sub-array of the transducer-array 50 is provided will now be described.

The sampling apparatus 100 samples the echo signal received from the transducer-array 50 by using a sampling frequency for extracting I component data and Q component data, and outputs the I component data and the Q component data extracted according to a result of the sampling to the diagnostic image generation apparatus 300. The I component data and the Q component data may be decimated data, but they are not limited thereto.

The sampling apparatus 100 may output the I component data and the Q component data to the diagnostic image generation apparatus 300 via wire transmission (for example, a PCI, a PCI-express, or a USB), wireless transmission (for example, Wifi or Zigbee), or the like.

The diagnostic image generation apparatus 300 generates a diagnostic image by using the I component data and the Q component data output from the probe 200. The diagnostic image generation apparatus 300 according to the present exemplary embodiment may be implemented based on a CPU or a GPU in a back-end system, a mid-end system, a general-use computer system, or the like, but the diagnostic image generation apparatus 300 is not limited thereto. The diagnostic image according to the present exemplary embodiment may be an ultrasonic image, but the diagnostic image is not limited thereto.

The storage unit 310 stores the I component data and the Q component data output from the probe 200. Accordingly, the storage unit 310 may be a two-port memory including two input ports.

The storage unit 310 according to the present exemplary embodiment may distinguishably store the I component data and the Q component data output from each of a plurality of sampling apparatuses 100 included in the probe 200, but the storage unit 310 is not limited thereto. The storage unit 310 may include a plurality of storage spaces corresponding to the plurality of sampling apparatuses 100 included in the probe 200.

The storage unit 310 according to the present exemplary embodiment is a typical storage medium, and examples of the storage unit 130 may include a hard disk drive (HDD), a read only memory (ROM), a random access memory (RAM), a flash memory, and a memory card.

The time delay calculator 320 calculates a time delay value for coarse delay and a time delay value for fine delay. The time delay calculator 320 according to the present exemplary embodiment may calculate time delay values in consideration of a distance between a focusing point on the object and the transducer-array 50 that transmits a transmission signal, but the time delay calculator 320 is not limited thereto.

The time delay value for coarse delay may be applied between the storage unit 310 and the interpolator 330, and the time delay value for fine delay may be applied to the beamformer 340.

Accordingly, the time delay value for coarse delay calculated by the time delay calculator 320 is applied to each of the I component data and the Q component data that are to be transmitted from the storage unit 310 to the interpolator 330, and the time delay value for fine delay calculated by the time delay calculator 320 is applied to each of the I component data and the Q component data which are to be transmitted to the beamformer 340.

The time delay calculator 320 may calculate time delay values corresponding to the plurality of sampling apparatuses 100. In other words, the time delay calculator 320 may calculate time delay values corresponding to the channels or sub-arrays of the transducer-array 50.

The interpolator 330 interpolates the I component data and the Q component data for each of the plurality of channels or sub-arrays output from the storage unit 310. In other words, the interpolator 330 may perform interpolation with respect to each of the channels or sub-arrays of the transducer-array 50.

For example, the interpolator 330 may apply the time delay value for coarse delay to the I component data and the Q component data output from the storage unit 310, and the interpolator 330 may also up-sample each of the I component data and the Q component data by using an interpolation filter. However, the interpolator 330 according to the present exemplary embodiment may not up-sample each of the I component data and the Q component data in some cases.

The beamformer 340 performs beamforming on the I component data and the Q component data for each of the plurality of channels or sub-arrays output from the interpolator 330. For example, the beamformer 340 may be a phase-rotation beamformer, but it is not limited thereto.

The mid-processing unit 350 may perform mid-processing on the I component data and the Q component data output from the beamformer 340, and the echo processing unit 360 may perform echo processing on data output from the mid-processing unit 350.

The beamformer 340, the mid-processing unit 350, and the echo processing unit 360 of FIG. 4B may perform the operations performed in the beamformer 340, the mid-processing unit 350, and the echo processing unit 360 of FIG. 4A, so a duplicate description will not be provided here.

The display unit 370 displays a diagnostic image output from the echo processing unit 360. For example, the display unit 370 may be any type of output device, such as a display panel, an LCD monitor, and a monitor, included in the diagnostic image generation apparatus 300.

However, it will be understood by one of ordinary skill in the art to which the present embodiment pertains that the diagnostic image generation apparatus 300 according to the present exemplary embodiment may not include the display unit 370 but may include an output unit (not shown) for outputting the diagnosis image generated by the diagnostic image generation apparatus 300 to an external display unit (not shown).

Accordingly, the diagnostic image generation apparatus 300 may obtain sampling data for the echo signal reflected from the object by using the probe 200, while reducing hardware complexity. The diagnostic image generation apparatus 300 may generate a real-time high-resolution diagnosis image from the sampling data and display the diagnostic image.

In addition, since the diagnostic image generation apparatus 300 may be implemented based on software in an end-user terminal such as a general-use computer system or a portable terminal, a diagnostic image may be conveniently generated using the data output from the integrated probe 200.

Figure 5:
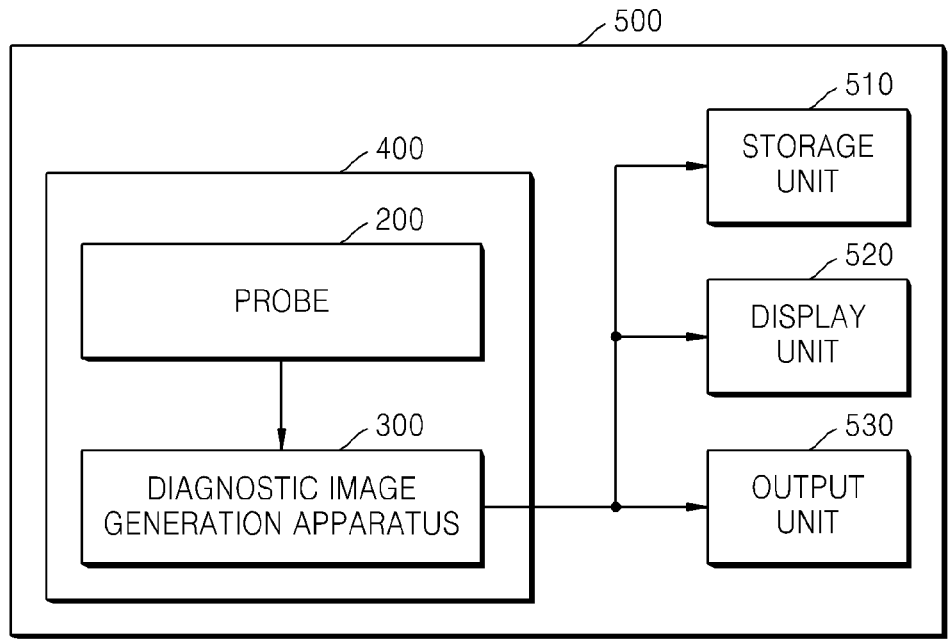
FIG. 5 is a block diagram of a medical imaging system according to an exemplary embodiment.

FIG. 5 is a block diagram of a medical imaging system 500 according to an exemplary embodiment. Referring to FIG. 5, the medical imaging system 500 may include a diagnostic system 400, a storage unit 510, a display unit 520, and an output unit 530. The diagnostic system 400 may include a probe 200 and a diagnostic image generation apparatus 300.

The diagnostic system 400 of FIG. 5 may correspond to the exemplary embodiment of the diagnostic system 400 of FIG. 4B. Accordingly, matters described above with reference to FIG. 4B may be applied to the diagnostic system 400 of FIG. 5, so a detailed description thereof will not be provided here.

FIG. 5 illustrates only components of the medical imaging system 500 that are associated with the present exemplary embodiment. Accordingly, it will be understood by one of ordinary skill in the art to which the present exemplary embodiment pertains that the medical imaging system 500 may further include general-use components other than the components illustrated in FIG. 5.

The diagnostic system 400 may generate a diagnostic image for diagnosing an object, by using the probe 200 and the diagnostic image generation apparatus 300.

The probe 200 samples an echo signal reflected from the object by using a sampling frequency for extracting I component data and Q component data, and outputs I component data and Q component data extracted according to a result of the sampling.

At this time, the probe 200 may alternately extract the I component data and the Q component data for the echo signal by sampling the echo signal, and output the extracted I component data and the extracted Q component data.

The diagnostic image generation apparatus 300 generates a diagnostic image of the object by using the I component data and the Q component data output from the probe 200.

The storage unit 510 stores the diagnostic image generated by the diagnostic image generation apparatus 300, and the display unit 520 displays the diagnostic image. However, it will be understood by one of ordinary skill in the art to which the present exemplary embodiment pertains that the medical imaging system 500 according to the present exemplary embodiment may not include the display unit 520 but may include an output unit 530 for outputting the diagnosis image generated by the diagnostic image generation apparatus 300 to an external display unit (not shown).

The output unit 530 outputs the diagnostic image generated by the diagnostic image generation apparatus 300 to an external device via a wire-wireless network, wire serial communication, or the like. The output unit 530 may transmit data to and receive data from an external device via a wire-wireless network, wire serial communication, or the like, and a network according to the present exemplary embodiment may be the Internet, a local area network (LAN), a wireless LAN, a wide area network (WAN), a personal area network (PAN), or the like, but the network is not limited thereto. The network may be any of various other types of networks capable of transmitting and receiving data.

Accordingly, it will be understood by one of ordinary skill in the art to which the present exemplary embodiment pertains that the storage unit 510 and the output unit 530 according to the present exemplary embodiment may be integrated into a picture archiving communication system (PACS) by further including an image reading and searching function.

Accordingly, the medical imaging system 500 according to the present exemplary embodiment may provide a user with a high-definition 3D diagnostic image generated using the integrated smart probe 200.

Although the sampling apparatus 100 is included in the probe 200 in FIGS. 4B and 5, the sampling apparatus 100 is not limited thereto. The sampling apparatus 100 may be included in the diagnostic image generation apparatus 300.

Figure 6:
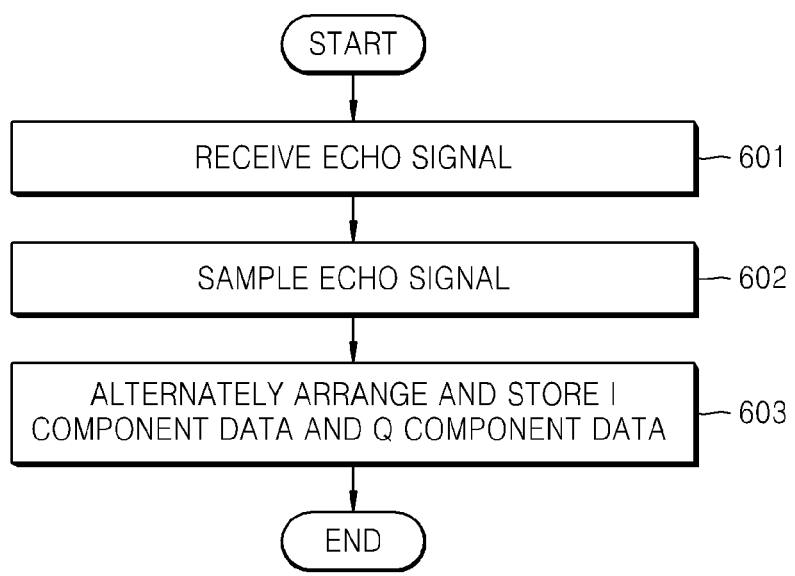
FIG. 6 is a flowchart of a sampling method according to an exemplary embodiment.

FIG. 6 is a flowchart of a sampling method according to an exemplary embodiment. Referring to FIG. 6, the sampling method includes operations sequentially performed in the sampling apparatus 100, the reception beamforming apparatus 40, the diagnostic system 400, or the medical imaging system 500 shown in FIGS. 1, 3A, 3B, 4A, 4B, and 5. Accordingly, matters described above with reference to the sampling apparatus 100, the reception beamforming apparatus 40, the diagnostic system 400, or the medical imaging system 500 shown in FIGS. 1, 3A, 3B, 4A, 4B, and 5 may be applied to the sampling method of FIG. 6 although they are not described here.

In operation 601, the echo signal reception unit 110 receives an echo signal reflected from an object.

In operation 602, the sampling unit 120 samples the echo signal received in operation 601, by using a sampling frequency for extracting I component data and Q component data from the echo signal. For example, the sampling frequency may be a minimum sampling frequency based on the sampling theory.

In operation 603, the storage unit 130 alternately arranges and stores the I component data and the Q component data extracted according to a result of the sampling in operation 602.

Thus, in the sampling method according to the present exemplary embodiment, the I component data and the Q component data may be extracted directly from the echo signal without performing demodulation, whereby hardware complexity may be reduced while generating a real-time high-resolution diagnostic image. In addition, the real-time high-resolution diagnostic image may be generated while the amount of sampled data is still reduced.

When the sampling apparatus 100 is combined with the transducer-array 50 and is implemented in the probe 200, a beamforming and signal-processing algorithm based on software may be implemented in a general-use computer system including the diagnostic image generation apparatus 300. Accordingly, an ultrasonic imaging system that is reconfigurable and programmable may be implemented.

In this case, an optimized system development environment may be provided to researchers and developers of an ultrasound algorithm or to image analysis engineers (IAEs) who analyze ultrasonic images, whereby an ultrasonic imaging apparatus rapidly responding to customers' demands may be realized.

Therefore, by using the sampling method according to the present exemplary embodiment, the utility of a 3D ultrasonic imaging apparatus using a 2D array-transducer is much enhanced, and thus a real-time 3D ultrasonic image of an object may be obtained and clinical information such as a 3D color flow image of a heart, may be provided.

As described above, according to one or more of the above exemplary embodiments, when an echo signal reflected from an object is sampled to generate a diagnostic image of the object, the echo signal may be efficiently sampled while reducing hardware complexity.

The above-described method can be written as one or more computer programs and can be implemented in general-use digital computers that execute the programs using a computer readable recording medium. A structure of the data used in the above-described method may be recorded in a computer-readable recording medium through several methods. Examples of the computer readable recording medium include magnetic storage media (e.g., ROM, RAM, USB, floppy disks, hard disks, etc.), optical recording media (e.g., CD-ROMs, or DVDs), and a PC Interface (for example, PCI, PCI-express, and Wifi).

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

What is claimed is:

1. A sampling method comprising:
   receiving an echo signal reflected from an object;
   sampling the received echo signal by using a sampling frequency to extract in-phase (I) component data and quadrature (Q) component data; and
   alternately and sequentially arranging and storing the I component data and the Q component data extracted according to a result of the sampling in a repeated pattern.

2. The sampling method of claim 1, wherein the sampling frequency is a minimum sampling frequency based on the sampling theory.

3. The sampling method of claim 1, wherein the sampling of the received echo signal comprises sampling the received echo signal by using a sampling frequency corresponding to 4 times a center frequency of a transducer for transmitting a transmission signal to the object.

4. The sampling method of claim 1, wherein the sampling of the received echo signal comprises sampling the received echo signal by using a sampling frequency corresponding to 4 times any one of a frequency of the received echo signal and a frequency of a transmission signal transmitted by a transducer to the object.

5. The sampling method of claim 1, wherein the sampling of the received echo signal comprises alternately extracting I component data and Q component data of the received echo signal by sampling the received echo signal.

6. The sampling method of claim 1, wherein the alternately arranging and storing of the I component data and the Q component data comprises receiving the I component data and the Q component data via a single port and sequentially and alternately arranging and storing the received I component data and the received Q component data.

7. The sampling method of claim 1, further comprising:
   reading the stored I component data and Q component data in an interleaving manner; and
   decimating the read I component data and the read Q component data.

8. The sampling method of claim 1, further comprising:
   transmitting the stored I component data and Q component data, or data decimated from the stored I component data and Q component data.

9. A non-transitory computer-readable recording medium having recorded thereon a computer program, which when executed by a computer, performs the sampling method of claim 1.

10. A sampling apparatus comprising:
    an echo signal reception unit which receives an echo signal reflected from an object;
    a sampling unit which samples the received echo signal by using a sampling frequency to extract in-phase (I) component data and quadrature (Q) component data; and a storage unit which alternately and sequentially arranges and stores the I component data and the Q component data extracted according to a result of the sampling in a repeated pattern.

11. The sampling apparatus of claim 10, wherein the sampling frequency is a minimum sampling frequency based on the sampling theory.

12. The sampling apparatus of claim 10, wherein the sampling unit samples the received echo signal by using a sampling frequency corresponding to 4 times any one of a center frequency of a transducer for transmitting a transmission signal to the object, a frequency of the transmission signal, and a frequency of the received echo signal.

13. The sampling apparatus of claim 10, wherein the sampling unit alternately extracts I component data and Q component data of the received echo signal by sampling the received echo signal, and the storage unit receives the I component data and the Q component data via a single port and sequentially and alternately arranges and stores the received I component data and the received Q component data.

14. The sampling apparatus of claim 10, further comprising an analog beamformer which performs analog beamforming on the received echo signal,
wherein the sampling unit samples the analog beamformed echo signal.

15. The sampling apparatus of claim 10, further comprising an outputting unit which outputs the stored I component data and Q component data, or data decimated from the stored I component data and Q component data via wireless transmission.

16. A reception beamforming apparatus comprising:
a sampling unit which samples an echo signal for each of a plurality of channels by using a sampling frequency to extract I component data and Q component data, and outputs I component data and Q component data for each of the plurality of channels extracted according to a result of the sampling;
an interpolator which interpolates the output I component data and Q component data for each of the plurality of channels; and
a beamformer which performs beamforming with respect to I component data and the Q component data for each of the plurality of channels obtained by the interpolation in the interpolator to generate a beamformed signal for the I component data and a beamformed signal for the Q component data,
wherein the sampling unit alternately and sequentially extracts the I component data and Q component data for each of the plurality of channels by sampling an echo signal for each of the plurality of channels in a repeated pattern.

17. A probe comprising:
a transducer-array which receives an echo signal reflected from an object; and
a sampling unit which samples an echo signal received from the transducer-array by using a sampling frequency to extract I component data and Q component data, and outputs the I component data and the Q component data extracted according to a result of the sampling,
wherein the sampling unit alternately and sequentially arranges and stores the I component data and the Q component data extracted according to the result of the sampling in a repeated pattern, reads the stored I component data and the stored Q component data in an interleaving manner, and outputs the read I component data and the read Q component data.

18. A medical imaging system comprising:
a probe which samples an echo signal reflected from an object by using a sampling frequency to alternatively and sequentially extract I component data and Q component data in a repeated pattern, and outputs I component data and Q component data extracted according to a result of the sampling; and
a diagnostic image generation apparatus which generates a diagnostic image of the object by using the output I component data and the output Q component data.

* * * * *